United States Patent [19]

Gomez et al.

[11] 4,387,160

[45] Jun. 7, 1983

[54] IMMUNOCHEMICAL ASSAY FOR CREATINE KINASE-MB ISOENZYME

[75] Inventors: Magdalena U. Gomez, Wayne; Marvin L. Miller, West Orange; Richard W. Wicks, Belleville, all of N.J.

[73] Assignee: Hoffmann-La Roche Inc., Nutley, N.J.

[21] Appl. No.: 235,078

[22] Filed: Feb. 17, 1981

[51] Int. Cl.³ .................... G01N 33/54; C12Q 1/50
[52] U.S. Cl. .................................. 435/7; 435/17
[58] Field of Search ............ 435/7, 17, 810; 424/12

[56] References Cited

U.S. PATENT DOCUMENTS

| | | | |
|---|---|---|---|
| 3,843,443 | 10/1974 | Fishman | 435/180 |
| 3,932,221 | 1/1976 | Pfleiderer | 435/17 |
| 4,012,285 | 3/1977 | Pfleiderer | 435/7 |
| 4,067,775 | 1/1978 | Wurzburg et al. | 435/7 |
| 4,224,406 | 9/1980 | Gomez et al. | 435/7 |
| 4,298,592 | 11/1981 | Lin et al. | 435/17 |
| 4,353,982 | 10/1982 | Gomez et al. | 435/17 |

OTHER PUBLICATIONS

Jockers-Wreton et al., Clin. Chim. Acta., 58, 223-232, (1975).

*Primary Examiner*—Esther M. Kepplinger
*Attorney, Agent, or Firm*—Jon S. Saxe; George M. Gould; William H. Epstein

[57] ABSTRACT

An immunochemical process and test kit for determining accurately the amount of creatine kinase-MB isoenzyme (CK-MB) in biological fluids employing two separate immunoassays to a single sample of the biological fluid. This process and test kit are useful in diagnosing myocardial infarct.

7 Claims, No Drawings

IMMUNOCHEMICAL ASSAY FOR CREATINE KINASE-MB ISOENZYME

BACKGROUND OF THE INVENTION

Creatine kinase (CK) occurs in animal body fluids and tissue in the form of three known isoenzymes, designated CK-BB, CK-MM and CK-MB. Each of these three isoenzymes, namely CK-BB, CK-MM, and CK-MB, differs one from the other by virtue of containing a different combination of subunits designated M or B. CK-BB has two B subunits, CK-MM has two M subunits, and CK-MB has one M and one B subunit. Determining the presence of CK-MB in biological fluids, especially in a patient's serum, has become very useful in the diagnosis of myocardial infarction. (Galen, RS., Human Path 6: No. 2, 145-147, Apr. 1975).

Current immunological methods for determining the presence of CK-MB and the disadvantages of such methods have recently been reported and reviewed (Current Problems in Cardiology, Vol. III, No. 12, March, 1979 p. 7-28). These methods have not been very satisfactory in resolving the difficulty of interference from CK-MM and CK-BB in distinguishing or determining CK-MB from CK-MM and CK-BB.

Immunological process for determining CK-MB activity in a sample of a biological fluid has been disclosed in U.S. Pat. Nos. 4,067,775 and 4,237,044. This disclosed process of these patents employs an antibody produced from an activated CK-MM antigen. In this process it is required that the fluid sample tested must not contain any CK-BB isoenzyme. In particularly U.S. Pat. No. 4,067,775 states in column 3 at lines 38-40 that "CK-BB interferes with the process of the invention and therefore must not be present in the biological fluids being tested". Since biological fluids contain CK-BB, the assay of these patents may require time consuming and difficult procedures to first remove any CK-BB from the fluid. If any CK-BB is in the fluid sample, false positive results would be produced through the use of this assay. Thus, this process cannot be employed to determine CK-MB in fluids containing CK-BB.

Wreton and Pfeiderer, Clinica Chimica Acta 58, 223-232 (1975) discloses an immunoassay system wherein CK-MM and CK-BB are determined by immunoinhibition and immunotitration assays. These assays require the quantitation of values obtained by comparing residual isoenzyme activity with total isoenzyme activity of the sample. An immunoinhibition assay for CK isoenzymes is one wherein the enzymatic activites of CK-isoenzymes are differentially inhibited or inactivated within a test sample immunologically by inhibiting or inactivating antibodies which maintain the homogeneity of the sample. The Wreton and Pfleiderer process requires a multiplicity of assays (at least four) to arrive at values needed to determine the CK-isoenzyme activities. There would, therefore, be correspondingly four sources of errors, along with an equal number of time consuming procedures.

A process disclosed by Wursburg et al. in J. Clin. Chem. Clin. Biochem. 15, 131-137 (1977) employs precipitating antibodies to differentiate CK-isoenzymes in a scheme which necessitates measurement from four different assays. The assays provide for measuring total CK activity in the test sample and residual activities after adding precipitating anti-CK-BB, precipitating unit-CK-MM and both of these precipitating antibodies to separate reaction vessels. By this process, homogeneity of the sample is not maintained by the precipitating antibodies. Like the Wreton-Pfleiderer process, this process requires laborous and time consuming multiple assays with correspondingly high sources of errors.

SUMMARY OF THE INVENTION

The present invention relates to a process and a diagnostic test kit system for quantitatively determining CK-MB isoenzyme, a form of creatine kinase which occurs in a biological fluid sample in a plurality of isoenzyme forms containing the subunit M or B or both.

In accordance with this invention it has been discovered that when a biological fluid sample is assayed by the following procedure:

(a) incubating in a first reaction vessel a first of two portions of a biological fluid sample with a first antibody which selectively binds immunologically the creatine kinase isoenzymes containing the M subunit by selective immunoinhibition of the M subunit in the first portion to inhibit the enzyme activity of only the M subunit of creatine kinase isoenzymes and thereafter quantitatively measuring the B subunit activity of the first portion; (b) incubating in a separate reaction vessel the second of two portions of the biological fluid sample with (i) an antibody which selectively binds immunologically the creatine kinase isoenzymes containing the M subunit and (ii) a precipitating second antibody which selectively binds immunologically with the antibody binding the creatine kinase isoenzymes containing the M subunit to form a reaction product of the second antibody with the other antibody and the creatine kinase isoenzymes containing the M subunit as a precipitate in the second portion and thereafter quantitatively measuring the B isoenzyme activity of the supernatant in the second portion; and (c) determining the CK-MB activity in the biological fluid sample from the measurements obtained from the first and second portions; one can rapidly and economically determine accurately the amount of CK-MB even in fluids containing CK-BB. This process of this invention does not require a multiplicity of assays or calculations which could lead to cumbersome and less accurate results.

This process is useful in the diagnosis of myocardial infarction.

DETAILED DESCRIPTION OF THE INVENTION

The present invention relates to a process for quantitatively determining CK-MB in any biological fluid. According to the process of the present invention, CK-MB can be determined using two portions obtained from a single sample of a biological fluid to provide two values for the activity of the B subunit in each of the portions. From these activities CK-MB activity can be determined.

For the invention processes it is possible to use biological fluids, e.g. whole blood, plasma, sera, lymph, bile, urine, spinal fluid, sputum, sweat and the like as well as stool excretions of humans or other animals. It is possible also to use fluid preparations of human or other animal tissue such as skeletal muscle, heart, kidney, lungs, brain, bone marrow, skin, and the like. The preferred biological fluid for the invention processes, however, is human serum. The serum in most cases need not be diluted for the invention processes but may be diluted for better results if the amount of CK is unusually high as in the serum of a patient suffering from an acute myocardial infarct.

Particularly the invention relates to a process for quantitatively determining the enzymatic activity of CK-MB isoenzyme in a biological fluid sample which may contain CK-MB, CK-MM and CK-BB. The process is achieved by (a) incubating in a first reaction vessel a first of two portions of a biological fluid sample with a first antibody which selectively binds immunologically with the creatine kinase isoenzymes containing the M subunit by selective immunoinhibition of the M subunit in the first portion to inhibit the enzyme activity of only the M subunit of creatine kinase isoenzymes and thereafter quantitatively measuring the B subunit activity of the first portion of the biological fluid sample, (b) incubating in a separate second reaction vessel the second of the two portions of the biological fluid sample with: (i) an antibody which selectively binds immunologically with the creatine kinase isoenzymes containing the M subunit and (ii) a precipitating second antibody which binds immunologically with the antibody binding the creatine kinase isoenzymes containing the M subunit to form a reaction product of the second antibody with the other antibody and the creatine kinase isoenzymes containing the M subunit as a precipitate in the second portion and thereafter quantitatively measuring the B isoenzyme activity in the supernatant of the second portion; and (c) determining the CK-MB activity in the biological fluid sample from the measurements obtained from the first and second portions.

The process of this invention employs two immunologic reactions, each reaction being carried out in separate reaction vessels. There is obtained from each of these two reactions a measurement of the enzymatic activity of the liquid in the reaction vessels. Each reaction may be performed simultaneously or may be carried out at different times. It is preferred that the reactions be carried out simultaneously. It is not essential that the reaction vessels contain equal portions of sample but equal portions are preferred for ease of quantitation. In order to determine and distinguish the enzymatic activity of CK-MB in the sample fluid, one needs only to quantitate by any acceptable procedure recognized in the art the values of the enzymatic activity obtained from the two separate reactions. For example, where the reaction vessels contain equal portions of sample, one need only to subtract the enzymatic activity determined in the second reaction vessel from the enzymatic activity determined in the first reaction vessel. Where the portions are unequal one needs merely to first correct for the differences in enzyme concentration, by an recognized procedure, before subtracting the values obtained for the two reaction vessels.

The reaction vessels used in the process of this invention may be any vessel recognized in the arts as suitable to carry out an immunologic assay. Among the available vessels suitable for carrying out the process of the invention are test tubes of glass or plastic or metal. The preferred reaction vessel is a glass test tube.

The invention also relates to a diagnostic test kit system for quantitatively determining the presence of CK-MB isoenzyme form of creatine kinase which occurs in a biological fluid in a plurality of isoenzyme forms containing subunit M or B or both. The constituents of the test kit system are: (a) a first container containing an antibody capable of selectively binding immunologically with the creatine kinase isoenzymes containing the M subunit by selective immunoinhibition of the M subunit, (b) a second container containing a precipitating second antibody capable of selectively reacting immunologically with the antibody contained in the first container, and (c) a reagent of enzyme-co-enzyme and substrate capable of determining the enzymatic activity of the B subunit.

When all the components of the diagnostic test kit system are used in accordance with the process of the invention as provided herein, one skilled in the art would be able to determine the enzymatic activity of CK-MB in a biological fluid sample containing CK-MB, CK-MM and CK-BB. The test kit would be suitable for clinics, hospitals, laboratories, and individual physicians having a need to determine and distinguish CK-MB in fluids.

In accordance with this invention the first antibody can be any antibody which selectively immunoinhibits the M subunit of CK without significantly immunoinhibiting the B subunit. These antibodies can be prepared in the conventional manner by injection of a purified CK-MM antigen into an animal and bleeding the animal to obtain the serum containing the antibody. Any of the conventional means which are known in the art can be used for purifying CK-MM antigen and for injecting this antigen into animals to obtain the antibody used in this invention. Among the antibodies that may be utilized are those of U.S. Pat. No. 4,237,044 raised in an animal species from CK-MM antigen which has been activated with an activator such as mercaptoethanol prior to innoculation as well as those raised from CK-MM antigen which has not been activated prior to innoculation such as those employed in the immunoinhibition assay of the aforementioned Wreton-Pfleiderer reference. While addition of the first antibody in the process of this invention may cause precipitation, the precipitation will not sediment but will remain homogeneous during the course of this process.

The first antibody may be produced in any animal species recognized in the art. The animal species include especially vertebrates, e.g. pig, cattle, dog, donkey, horse, goat, rabbit, rat and the like. Among these animals, mammals such as donkey, sheep and goat are preferred. The most preferred are goats.

In one preferred aspect of the invention, the first antibody is produced by immunizing goats, a first animal species, with a purified CK-MM and obtaining goat anti-(CK-MM), the first antibody, by conventional immunological techniques. This first antibody for use in this invention should be capable of selectively inhibiting the M subunit of CK by immunoinhibition. By immunoinhibition is meant that the first antibody will immunologically inhibit the M subunit without significantly inhibiting any B subunit, and that this inhibition of the M subunit occurs in the sample portions with maintenance of the homogeneity of the sample.

The first antibody is incubated and preferably mixed with the first and second of two portions, preferably equal portions, of test sample in the reaction vessels. As a result the first antibody binds immunologically any CK-MB and CK-MM of each portion of the sample to provide immunoinhibition of the CK-MB and CK-MM without significantly affecting the B subunit. It is to be noted that the important feature of the first antibody for the second portion is merely that the first antibody immunologically bind CK-MB and CK-MM without significantly binding CK-BB. It is not essential or necessary that the first antibody cause immunoinhibition in the second portion. As a result the first antibody can be replaced in the second portion by a different antibody, one raised from purified CK-MM antigen in an animal other than the animal used to raise the first antibody. In fact, the antibody utilized as the first antibody in the second portion may be any antibody which selectively binds the creatine kinase containing a M subunit without substantially inhibiting the B subunit.

The temperature and time of the incubation of each portion of the test sample after adding antibody are not critical and can be at any temperature and for any length of time recognized in the art as usual and suitable for carrying out enzyme immunoassays. Preferably the incubations are carried out at room temperature and from 5 to 60 minutes.

In accordance with this invention the measurement of the first portion for enzymatic activity after incubating said portion with first antibody is accomplished while homogeneity of said portion is maintained. In this manner of measurement, the B subunit of CK-MB and CK-BB can be determined.

The amount of first antibody used in the second portion of the sample is an amount sufficient to bind substantially all the CK-MB and CK-MM isoenzymes of the particular portion. For best results the first antibody is added to each of the sample portions in an amount in excess of that amount normally required to bind all the CK-MB and CK-MM. The determination of the amount of the first antibody needed for each portion can be determined by well recognized procedures in this art.

The second portion of the test sample in the second reaction vessel is treated with a precipitating second antibody, after adding another antibody either the first or a replacement antibody. The time of adding the second antibody after adding the first antibody is not critical with about five minutes being preferred. If so desired, longer periods of time may be utilized. In accordance with this invention the second precipitating antibody can be any antibody which selectively binds and precipitates the first antibody used in the second portion and which precipating antibody is substantially free of immunological activity against the B subunit form of creatine kinase.

The second antibody may be produced in any animal species, other than the animal species used to produce the other antibody to this reaction by any method recognized in the art. Typically the second antibody is produced by immunizing donkeys with goat gamma-globulin (IgG) and obtaining donkey anti-goat IgG by conventional immunological techniques. The second antibody, obtained in this manner is capable of binding any goat IgG, including therefore goat anti-(CK-MM), the preferred first antibody. The second antibody is preferably bound to a solid support and the resulting second antibody-solid support is incubated with the second portion of the test sample in the second reaction vessel, preferably after mixing, for approximately 5 minutes at room temperature. As a result the second antibody binds immunologically the other antibody in the second portion of the sample. This provides an immunoprecipitin containing CK-MB-first antibody-second antibody, CK-MM-first antibody-second antibody and first antibody-second antibody. The amount of second antibody used is an amount sufficient to bind all the first antibody. The second antibody is generally added in an amount in excess of that required to bind all the first antibody in accordance with the preferred embodiment of this invention.

In accordance with this invention, once the precipitate is formed in the second portion after adding the second antibody, the precipitate may be separated from the second portion by any conventional means known in the art, leaving a resulting supernatant which is measured for enzymatic activity. In accordance with this invention it is the supernatant which is measured for enzymatic activity.

Among the conventional means available for separating the precipitate from the second portion are conventional filtration and chromatographic methods. The most preferred method for separating the precipitate from the second portion is centrifugation followed by decanting the supernatant and measurement of the decanted supernatant.

The supernatant of the second portion is then conventionally measured to determine CK-BB isoenzyme activity of the supernatant by any art recognized process.

The measurement or determination of the activity of the inhibited CK-MB and/or CK-BB in each reaction portion of the test sample may be accomplished by any conventional methods recognized in the art. Among these methods are included colorimetric methods, as described, for example in "Methoden der enzymatischen Analyse", edited by H. U. Bergmeyer, 3rd edition (1974), Vol. 1, page 145 et seq. Also included is the determination of CK-BB fluorometrically. Creatine is liberated from creatine phosphate by CK and this creatine can be measured fluorometrically in a process developed by R. B. Conn, Clin, Chem., Vol. 6, page 537 et seq. (1960), by reaction with ninhydrin in a strongly alkaline solution.

Kinetic methods in which enzyme activity is determined by measurement in UV at, for example, 334, 340 or 366 nm are preferred for this purpose. Especially preferred is a standard method in which CK is determined using creatine phosphate and adenosine diphosphate, Z. Klin. Chem. Klin. Biochem., Volume 8, page 658 et seq. (1970) and Volume 10, page 182 (1972). Test packs for determining CK activity by this method are available commercially.

Typically in the preferred method the enzymatic activity of the inhibited CK-MB and/or CK-BB is followed by adding suitable enzymes, coenzymes and substrates whereby CK-BB catalyzes the reversible transfer of a phosphate group from creatine phosphate to adenosine diphosphate with the rate of the resulting adenosine triphosphate being measured using coupled reactions catalyzed by hexokinase and glucose-6-phosphate dehydrogenose. The activity of this latter enzyme in reducing nicotinamide adenine dinucleotide is followed spectrophotometrically by measuring the increase in absorbance at 340 nm, with the rate of change of absorbance being directly related to the activity of the inhibited CK-MB and/or CK-BB in any given portion of the test sample.

The isoenzyme namely CK-MM, employed as antigen to raise the first antibody, can be obtained from any suitable biological fluid such as blood serum or biological organ or tissue such as cardiac muscle, skeletal muscle, bone marrow, or any other organ tissue known to have this isoenzyme. The preferred source of this isoenzyme is animal skeletal muscle.

Purification of the aforementioned isoenzymes to a state of high purity before using them for raising antibodies is most advisable in order to diminish the presence of nonspecific antibodies. The isoenzymes may be purified by any conventional purification procedure recognized in the art for such purposes. The preferred purification procedure encompasses conventional art recognized procedures such as alcohol fractionation and anion exchange chromatography.

The degree of high purity of the isoenzymes used to raise the antibodies as well as the specificity of the resulting antibodies can be determined by currently acceptable practices in the art such as by immunodiffusion or electrophoretic techniques. The preferred method for purity of the isoenzymes is acrylamide gel electrophoresis.

The second antibody may be insolubilized by attaching the second antibody to an insoluble solid support material. Suitable solid support materials include water insoluble organic polymeric substances such as cellulose or other polysaccharide, a vinyl addition polymer or condensation polymer or a water soluble inorganic substance of polymeric nature, such as glass or silicone resins. On the other hand the second antibody may be adsorbed to the surface of a solid support such as polystyrene, polypropylene polyfluoroethylene or polyvinylidenefluoride. The method of attachment of the second antibody to the solid support is not critical and may include (1) covalently coupling the soluble second antibody to an insoluble polymerized form, such as by reaction with an insolubilizing agent; (2) physical entrapment of particles of the second antibody in the pores of a gel polymer such as a cross-linked polyacrylamide; or (3) by physical adsorption on an insoluble polymeric substance. Where a solid support is used the preferred embodiment is that the second antibody be attached by adsorption on activated polyvinylidenefluoride (Kynar) utilizing the general procedures well known in the art such as the procedure disclosed in U.S. Pat. No. 3,843,443.

The following examples further illustrate the invention but are not intended to restrict the invention in scope or spirit.

EXAMPLE I

CK-MM Purification

I. Homogenate

Approximately 1000 g of human skeletal muscle or heart tissue is thawed at 4° C. Excess fat is trimmed from the tissue which is thereafter cut into small (1 cm) pieces. The pieces of tissue are then homogenized in a blender with 1000–1500 ml of cold (4° C.) 0.05 M (hydroxy methyl) amino methane [Tris buffer] containing 1 mM mercaptoethanol pH 7.4. The resulting homogenate is centrifuged at 50,000 xg for 20 minutes at 4° C., producing as a precipitate a pellet. The resulting supernatant liquid is filtered through a scintered glass funnel and retained. The pellet is placed back in blender with 500–700 ml of Tris buffer and again homogenized, centrifuge at 50,000 xg again and the supernatant liquid pooled with first supernate after filtering, providing pooled supernates for Part II.

II. Ethanol Precipitation

Cold (4° C.) absolute ethanol is added to the pooled supernates of Part I above slowly at 4° C. to a final concentration of 50% (V/V) and then allowed to stir at 4° C. for 30 minutes. After this period the resulting mixture is centrifuged at 7000 xg for 15 minutes at 4° C. The resulting supernatant is retained and the precipitated pellet is discarded. Cold (4° C.) absolute ethanol is slowly added to the supernate until ethanol concentration is 70%. The resulting mixture is allowed to stir for 30 minutes at 4° C. and is again centrifuged at 7000 xg for 15 minutes at 4° C. The resulting pellet is resuspended in 500–700 ml of 0.05 M Tris buffer pH 7.4 containing 1 mM mercaptoethanol and 0.05 M NaCl.

III. Ion Exchange Chromatography (Batch method)

Diethylaminoethyl dextran anion exchange resin (DEAE Sephadex A-50) equilibrated with 0.05 M Tris pH 7.4 containing 0.05 M NaCl and 1 mM mercaptoethanol is added to the resuspended pellet of part II above and allowed to stir at 4° C. for 30 minutes. The suspension is filtered through Whatman #1 filter paper and washed with portions of 0.05 M Tris buffer pH 7.4 containing 1 mM mercaptoethanol until filtrate contains negligible CK activity. The filtrate is then concentrated to 300–500 ml using PM-10 filter membrane at 4° C. under pressure.

IV. Second Ethanol Precipitation

Cold absolute ethanol is added slowly to the concentrated filtrate of Part III until 50% concentration is achieved. The resulting mixture is allowed to stir 30 minutes at 4° C. and centrifuged at 7000 xg to provide a pellet. This supernate is retained and the pellet is discarded. Cold absolute ethanol is added slowly to the supernate until 70% concentration is achieved. The resulting mixture is again centrifuged at 7000 xg for 15 minutes and the resulting pellet is obtained and dissolved in a minimum volume of 0.05 M Tris pH 7.4 (e.g. 50–75 ml). This resulting mixture is dialyzed against 2000 ml of 0.05 M Tris pH 7.4 at 4° C. with 2 changes of buffer. A slight precipitate forming in the mixture on dialysis is removed after centrifugation and discarded, leaving a supernatant for use in Part V below.

V. Ion Exchange Chromatography (Column)

DEAE Sephadex A-50 is equilibrated with 0.05 M Tris pH 7.4 and a 2.6 cm×60 cm column is prepared and washed extensively with this buffer. The final supernatant of Part IV is applied to this column and eluted from the column at 4° C. at a flow rate of 30 ml/hour. 10 ml fractions are collected. Fractions are analyzed for CK activity and protein content. Pooled fractions containing the majority of CK-MM isoenzyme are dialyzed against 0.05 M Tris pH 7.4 containing 10 mM ethylenediamine tetra-acetic acid (EDTA). The dialyzed fractions are concentrated using a PM-10 filter membrane at 4° C. under pressure to a suitable concentration (e.g. 8–40 mg protein/ml), and stored at 4° C. in 0.05 M Tris buffer pH 7.5 containing 10 mM EDTA. A slight precipitate which forms on standing is removed by centrifugation. Purity of the CK-MM in the stored material as determined by polyacrylamide gel electrophoresis is typically 90–100%. Electrophoresis on agarose gels is used to demonstrate the absence of MB and BB isoenzymes in the stored material which constitutes the finally purified sample of CK-MM.

EXAMPLE 2

Goat anti CK-MM Serum

In order to prepare the immunogen for immunizing goats, the purified CK-MM obtained from the procedure of Example I is diluted to 4 mg/ml in 0.02 M Tris buffer pH 7.5 and mixed with an equal volume of complete Freund's adjuvant (a mineral oil suspension containing killed M-tuberculosis bacilli). The resulting mixture is homogenized to produce an aqueous/oil emulsion which constitutes the immunogen. Goats were immunized weekly with an injection of 1 ml of immunogen subcutaneously into the auxiliary regions at two sites, each site receiving 0.5 ml of the immunogen. The goats were bled every two weeks to provide goat anti CK-MM serum.

EXAMPLE 3

Activation of Polyvinylidene Fluoride

In order to couple globulin fraction of donkey anti goat IgG serum to polyvinylidene fluoride (PVF), the PVF is first activated by the following procedure:

1. 15 liters of Tis-azide buffer is prepared by dissolving 36.3 g. of Tris (hydroxymethyl) aminoethane (Trizma base) and 15.0 g of sodium azide in approximately 14,000 ml of deionized water at room temperature and adjusting pH to 7.5±0.1 with 5 N HCl which has been prepared by diluting 50 ml of 38% HCl with 70 ml of deionized water. The volume of the resulting solution is adjusted to 15,000 ml with deionized water and store at room temperature.

2. 100 g of polyvinylidene fluoride powder is mixed with 600 ml of 2-propanol in a suitable vessel. The resulting suspension is homogenized in an homogenizer for 30 seconds at a speed setting for making a fine dispersion, providing a mixture which is transferred to a 4 liter graduated cylinder and allow to stand ten minutes at room temperature. 3400 ml of saline prepared by dissolving 28.9 g NaCl in 3400 ml deionized water is added to the mixture. After the addition of saline, the resulting mixture is mixed well and allowed to settle for one hour or until polyvinylidene fluoride has settled to approximately one-fifth of the total volume. The supernate is removed by aspiration and volume is increased back to 4000 ml with deionized water. Again the polyvinylidene fluoride is allowed to settle and the supernate is aspirated. Thereafter the volume is brought back to 4000 ml and the polyvinylidene fluoride is washed three more times in this manner with deionized water. Subsequently the polyvinylidene fluoride is washed two more times in the preceding manner with Tris-azide buffer from step 1. After the final wash, the volume of polyvinylidene fluoride is brought to 2000 ml and stored as a suspension at room temperature until used for coupling to donkey anti goat IgG serum.

EXAMPLE 4

Preparation of Globulin fraction of Donkey anti Goat IgG Serum

The globulin fraction of donkey anti goat IgG serum for use in coupling to activated PVF obtained according to Example 3 is prepared using the following ingredients and procedure:

| Item | Ingredient | Quantity |
|---|---|---|
| (a) | Donkey anti Goat IgG serum obtained commercially | 100 ml |
| (b) | Saturated ammonium sulfate solution prepared by adding 500 g of solid ammonium sulfate (granular) to 500 ml of deionized water and stirring vigorously at room temperature for one hour. Store at 4 C. and allow crystals to settle out. | 110 ml |
| (c) | 0.02 M Tris-azide buffer pH 7.5 | approx. 6 l |
| (d) | Saturated barium chloride solution prepared by adding 50 g of BaCl$_2$—2H$_2$O (granular) to 100 ml of deionized water, stirring vigorously for one hour at room temperature and allowing crystals to settle out. Store at room temperature. | approx. 1 ml |

PROCEDURE:

1. 100 ml of donkey anti goat IgG serum (item a) is placed in a suitable vessel at 4° C. on a magnetic stir plate. There is then added to the vessel slowly with moderate stirring 60 ml of saturated ammonium sulfate (item b) to bring the contents of the vessel to 37.5% saturation. The vessel is allowed to stir for one hour at 4° C., and thereafter the precipitated antibody is collected as a pellet by centrifugation at 1200 g for 30 minutes at 4° C. The pellet is dissolved in approximately 70 ml of Tris-azide buffer (item c) and the volume is brought to original 100 ml with the same buffer. Thereafter 50 ml of saturated ammonium sulfate (item b) is added slowly with moderate stirring at 4° C. to bring the resulting mixture to 33% saturation. The mixture is allowed to stir for one hour at 4° C. The precipitated antibody as a pellet from the mixture is obtained after centrifugation at 1200 g for 30 minutes at 4° C. The pellet is dissolved in approximately 40 ml of Tris-azide buffer (item c), and transferred to a dialysis bag and dialyzed against the Tris-azide buffer at 4° C. The buffer is changed three times (2 liters per change) after a minimum of four hours dialysis each time. The presence of any sulfate ions is determined by adding 1 ml of the dialyzate to 1 ml of saturated BaCl$_2$, mixing well and observing any appearance of a white precipitate which indicates the presence of sulfate. If any precipitate is observed change dialyzate with fresh buffer and continue until sulfate test is negative. The volume of the dialyzate is brought back to 100 ml with the Tris-azide buffer and centrifuged for 10 minutes at 2000 g at 4° C., collecting the supernatant. The supernate(s) containing the prepared donkey anti-goat IgG is stored at 4° C. until ready for coupling to the activated polyvinylidene fluoride obtained in Example 3.

EXAMPLE 5

Coupling of globulin fraction of Donkey anti goat IgG serum to activated polyvinylidene fluoride The coupling of the globulin fraction of donkey anti goat IgG serum prepared by process of Example 4 to a suspension of activated PVF prepared by the process of Example 3 is accomplished using the following ingredients and procedure:

| Item | Ingredient | Quantity |
|---|---|---|
| (a) | Activated polyvinylidene flouride (Example 3) | 2000 ml |
| (b) | Globulin fraction of Donkey Anti Goat (IgG) serum (Example 4) | 100 ml |
| (c) | Tris(hydroxymethyl)aminomethane (Trizma base) | 24.2 g |
| (d) | Disodium ethylenediamine tetraacetate (EDTA) | 147.4 g |
| (e) | 10N Sodium hydroxide in water | approx. 20 ml |

Procedure:

1. 10 liters of Tris-EDTA buffer was prepared as follows: Dissolve 24.2 g Trigma base (item a), 10.0 g sodium azide and 147.4 g EDTA (item d) in approximately 9000 ml of deionized water at room temperature. EDTA may require continuous stirring for 30–60 minutes until complete solution is achieved. The pH of the solution was adjusted to 7.5±0.1 with 10 N.NaDH and the solution adjusted to a volume of 10,000 ml with deionized water and store at room temperature.

2. 2000 ml of activated polyvinylidene fluoride suspension (item a) was placed in a suitable vessel and stirred at a moderate speed. 100 ml of donkey anti goat serum (item b) was added to the suspension and allow to stir for 6 hours at room temperature and overnight (12–18 hours) at 4° C., resulting in donkey anti goat IgG antibody coupled polyvinylidene fluoride.

3. The antibody coupled polyvinylidene fluoride of step 2 above was collected as a pellet by centrifugation at 1500 g for 10 minutes at 4° C. The supernate(s) were poured off leaving the pellet which was thoroughly resuspend in a total volume of 2000 ml of the Tris-EDTA buffer as prepared in step 1 above.

4. Step 3 was repeated for a total of 3 more times.

5. The final pellet(s) obtained after step 4 was resuspended in Tris-EDTA buffer (step 1) up to a volume of 500 ml, and 2.5 g of bovine serum albumin were dissolved in this suspension by moderate stirring for 30 minutes. This suspension was then homogenized in an homogenizer for 30 seconds at a speed setting for making a fine dispersion to provide as product insoluble anti goat IgG.

6. The insoluble anti goat IgG product was stored at 4° C. in the following final concentrations:

20% (w/v) polyvinylidene fluoride
0.02 M Tris pH 7.5
0.1% (w/v) sodium azide
0.5% (w/v) BSA
39.6 mM EDTA

EXAMPLE 6

A determination of CK-MB activity in biological fluid is accomplished by the following procedure which employs two test tubes:

1. To test tube one is added: 200 µl patient's serum and 250 µl goat anti CK-MM serum (as prepared by Example 2), with gentle mixing and then standing for 20 minutes at room temperature to provide the resulting mixture for step 3. 2. To test tube two is added: 200 µl patient's serum and 50 µl anti CK-MM serum (as prepared by Example 2) with gentle mixing and then standing for 5 minutes at room temperature. Thereafter 200 µl, the stored insoluble anti goat IgG prepared by Example 5 is added, mixed gently and allow to stand 5 minutes at room temperature. The tube is then centrifuged 5 minutes at 1000 xg, and the supernatant obtained for use in step 3.

3. 100 µl of the resulting mixture from step 1 and 200 µl of the supernatant from step 2 are added respectively to separate first and second portions of 1.0 ml of enzymatic CK reagent (Example 7) for measurement of CK-enzyme activity. Afterwards each portion is mixed thoroughly and allowed to incubate at 37° C. for 5 minutes. Absorbance is recorded for each portion at 340 nm at periodic intervals for a total of 5 minutes in a spectrophotometer at 37° C. using 1.0 cm pathlength cuvettes. The absorbance readings are converted to change in absorbance per minute, IU/liter of CK activity is obtained for each portion. Thereafter the CK activity value for the second portion is subtracted from the CK activity value for the first portion.

EXAMPLE 7

Enzymatic CK reagents of Example 7 contains the following ingredients:

| Active Ingredients | Concentration as Formulated |
| --- | --- |
| Creatine phosphate | 17 mM |
| D-Glucose | 20.0 mM |
| ADP | 1.2 mM |
| AMP | 8 mM |
| NAD (yeast) | 2.3 mM |
| $MgCl_2$ | 15 mM |
| Hexokinase (yeast) | 2500 IU/liter at 30° C. |
| Glucose-6-phosphate dehydrogenase (Leuconostoc) | 2500 IU/liter at 30° C. |
| Dithioerythritol | 60 mM |

The reagent ingredients are formulated in piperazine-N,N-bis(2-ethanesulfonic acid) buffer, pH 5.8±0.15 (30° C.).

What is claimed is:

1. A process for quantitatively determining in a biological fluid sample the presence of creatine kinase-MB isoenzyme where the creatine kinase can occur in biological fluids in a plurality of isoenzyme forms containing the subunit M or B or both, the process comprising:
   a. incubating in a first reaction vessel a first of two portions of the biological fluid sample with a first antibody which selectively binds immunologically with the creatine kinase isoenzymes containing the M subunit by selective immunoinhibition of the M subunit in the first portion of the sample and thereafter quantitatively measuring the B isoenzyme activity of the first portion of the sample,
   b. incubating in a separate reaction vessel the second of two portions of the biological fluid sample with:
      (i) an antibody which selectively binds immunologically with the creatine kinase isoenzymes containing the M subunit in the second portion sample; and
      (ii) a second antibody which selectively binds immunologically to form a solid phase with the antibody binding the creatine kinase isoenzymes containing the M subunit,
   to produce as a precipitate the reaction product of said second antibody with said other antibody and said creatine kinase isoenzymes containing the M subunit and thereafter quantitatively measuring the B isoenzyme activity of the supernatant in said second portion; and
   c. determining the CK-MB activity in said sample from said measurements through the substraction of the measurement obtained in the second portion, from the measurement obtained in the first portion.

2. A process according to claim 1 wherein the biological fluid sample is blood serum.

3. A process according to claim 1 wherein the first antibody of step (a) and the antibody binding the creatine kinase isoenzyme containing the M subunit of step (b) are goat anti-creatine kinase-MM, and the second antibody of step (b) is donkey anti-goat IgG.

4. A process according to claim 1 wherein the second antibody is bound to a solid support.

5. A process according to claim 4 wherein the solid support is polyvinylidenefluoride.

6. A process according to claim 1 wherein the enzymatic activity of B isoenzyme is determined by a spectrophotometric assay.

7. A process according to claim 6 wherein the spectrophotometric assay comprises: an enzyme-co enzyme and substrate mixture.

* * * * *